United States Patent
Corbera-Arjona et al.

(10) Patent No.: US 7,300,937 B2
(45) Date of Patent: Nov. 27, 2007

(54) DERIVATIVES OF CYANO-ARYL (OR CYANOHETEROARYL)-CARBONYL-PIPERAZINYL-PYRIMIDINES, THEIR PREPARATION AND APPLICATION AS MEDICATION

(75) Inventors: Jordi Corbera-Arjona, Barcelona (ES); David Vano-Domenech, Barcelona (ES); Maria Neus Mesquida-Estevez, Barcelona (ES); Jordi Frigola-Constansa, Barcelona (ES)

(73) Assignee: Laboratorios del Dr. Esteve, S.A. (ES)

( * ) Notice: Subject to any disclaimer, the term of this patent is extended or adjusted under 35 U.S.C. 154(b) by 29 days.

(21) Appl. No.: 10/312,195

(22) PCT Filed: Oct. 10, 2001

(86) PCT No.: PCT/ES01/00378

§ 371 (c)(1),
(2), (4) Date: Dec. 17, 2002

(87) PCT Pub. No.: WO02/32880

PCT Pub. Date: Apr. 25, 2002

(65) Prior Publication Data

US 2004/0048872 A1    Mar. 11, 2004

(51) Int. Cl.
*A61K 31/496* (2006.01)
*C07D 403/04* (2006.01)

(52) U.S. Cl. .............. 514/252.14; 514/252.18; 514/252.2; 544/295

(58) Field of Classification Search ........... 514/252.14, 514/252.18, 252.2; 544/295
See application file for complete search history.

(56) References Cited

U.S. PATENT DOCUMENTS

| | | | |
|---|---|---|---|
| 4,542,136 A | 9/1985 | Carminati et al. | 514/252 |
| 4,547,505 A | 10/1985 | Oepen et al. | 514/255 |
| 4,668,687 A * | 5/1987 | Yevich et al. | 514/252.19 |
| 5,128,343 A | 7/1992 | Pinol et al. | 514/252 |
| 5,162,323 A | 11/1992 | Frigola-Constansa et al. | 514/252 |
| 5,382,586 A | 1/1995 | Merce-Vidal et al. | 514/254 |
| 6,372,746 B1 * | 4/2002 | Corbera-Arjona et al. | 514/252.14 |

FOREIGN PATENT DOCUMENTS

| | | |
|---|---|---|
| EP | 0115713 | 8/1984 |
| EP | 0382637 | 8/1990 |
| EP | 0497659 | 8/1992 |
| EP | 0429360 | 10/1993 |
| ES | 2034909 | 4/1993 |
| JP | 04202185 | 7/1992 |
| WO | 99/05121 | 2/1999 |
| WO | 99-05121 | * 12/1999 |

OTHER PUBLICATIONS

C. Hill-Venning et al., "The Anaesthetic Action and Modulation of $GABA_A$ Receptor Activity by the Novel Water-soluble Aminosteroid Org 20599", *Neuropharmacology*, 35(9/10) pp. 1209-1222 (1996).

* cited by examiner

*Primary Examiner*—James O. Wilson
*Assistant Examiner*—Tamthom N Truong
(74) *Attorney, Agent, or Firm*—Ostrolenk, Faber, Gerb & Soffen, LLP

(57) ABSTRACT

New derivatives of cyanoaryl (or cyanoheteroaryl)-carbonyl-piperazinyl-pyrimidines (I), where $R_1$ represents an $OR_3$ radical, where $R_3$ represents a radical derived from a saturated hydrocarbon, with a linear or branched chain of 1 to 4 carbon atoms, and $R_2$ represents a phenyl radical substituted at least by one cyan radical (—C≡N), or a radical of a heteroaromatic ring of 5 or 6 members substituted at least by one cyan radical (—C≡N); and their physiologically acceptable salts, are useful for application in human and/or veterinary therapeutics as sedatives, anticonvulsants, hypnotics and general anaesthetics (I)

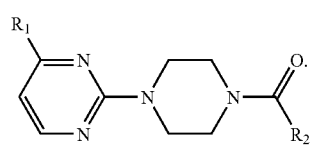

20 Claims, No Drawings

DERIVATIVES OF CYANO-ARYL (OR CYANOHETEROARYL)-CARBONYL-PIPERAZINYL-PYRIMIDINES, THEIR PREPARATION AND APPLICATION AS MEDICATION

FIELD OF THE INVENTION

The present invention relates to new cyanoaryl (or cyanoheteroaryl)-carbonyl-piperazinyl-pyrimidines, with the general formula (I), as well as to their physiologically acceptable salts, to their preparation procedures, their application as medicines in human and/or veterinary therapeutic use and the pharmaceutical compositions which contain them.

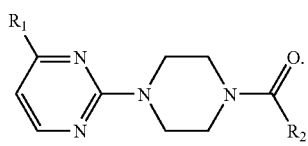

(I)

The new compounds object of the present invention may be used in the pharmaceutical industry as intermediates and to prepare medications.

BACKGROUND OF THE INVENTION

In our patent application WO 99/05121 we describe several derivatives of acyl-piperazinyl-pyrimidines, among which are the compounds with general formula (I), as products with sedative, anticonvulsive, hypnotic and general anaesthetic activity. In said patent derivatives are described with the general formula (I), in which $R_2$ represents, among others, an aryl radical and a heteroaryl radical. The term "aryl" represents a phenyl radical, not substituted or substituted by 1, 2 or 3 like or different substituents, such as fluorine, chlorine, bromine, amine, acetamide, nitro, methyl, trifluoromethyl or methoxy. The term "heteroaryl" represents a heteroaromatic ring substituted or not substituted with 5 or 6 fused heteroaromatic systems or members substituted or not, of 9 to 10 members comprising 1 or 2 heteroatoms such as nitrogen, oxygen or sulphur, with the substituents being groups such as fluorine, chlorine, bromine, amine, acetamide, nitro, methyl, trifluoromethyl or methoxy.

We have now discovered that introducing a cyan group (—C≡N) in aryl or heteroaryl radicals results in new compounds with the general formula (I) which are more powerful than those previously described, having interesting biological properties which make them particularly suitable for use in human and/or veterinary therapeutics. The compounds object of this invention are useful as agents which are active in the central nervous system of mammals, including man. Specifically, the new compounds are useful as sedatives, anticonvulsives, hypnotics and general anaesthetics.

DETAILED DESCRIPTION OF THE INVENTION

The present invention provides new compounds with the following properties: sedative, anticonvulsive, analgesic, muscular relaxant, antitussive, anxiolytic, antipsychotic, antidepressive, anti cerebral ischaemic, antimigraine, for sleep disorders, for neurodegenerative diseases, cognitive disorders and Alzheimer's disease, hypnotic or general anaesthesia in mammals, including man. Specifically, the new compounds of the invention are capable of causing conscious sedation, acting as hypnotic agents and agents capable of bringing about or maintaining general anaesthesia, depending on the dose and form of administration.

The compounds object of the present invention have the general formula (I)

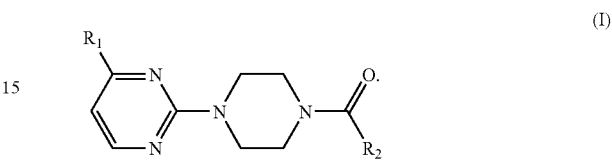

where $R_1$ represents an alkoxy radical and $R_2$ represents a cyanoaryl or a cyanoheteroaryl radical.

In the present invention the term "alkoxy" represents an $OR_3$ radical, where $R_3$ is alkyl $C_1$-$C_4$ (i.e., an alkyl radical deriving from a saturated hydrocarbon with a linear or branched chain with 1 to 4 carbon atoms), such as methoxy, ethoxy, propoxy, isopropoxy, butoxy, sec-butoxy or tert-butoxy.

The term "cyanoaryl" represents a phenyl radical substituted with at least one cyano radical (—C≡N).

The term "cyanoheteroaryl" represents a radical of a heteroaromatic ring with 5 or 6 members or of fused heteroaromatic members or systems, substituted or not, with 9 to 10 members, comprising 1 or 2 heteroatoms such as nitrogen, oxygen or sulphur, all of them substituted at least by a cyano radical (—C≡N), such as, 3-cyano-2-furyl, 3-cyano-2-thienyl, 5-cyano-2-thienyl, 3-cyano-2-pirrolyl, 3-cyano-2-pyridyl, 2-cyano-3-pyridyl, 2-cyano-4-pyridyl, 3-cyano-2-indolyl, 2-cyano-3-indolyl, 3-cyano-2-benzo[b]thienyl or 2-cyano-3-benzo[b]thienyl.

The present invention also relates to the physiologically acceptable salts of the compounds with the general formula (I), particularly to the salts from addition of mineral acids such as hydrochloric acid, hydrobromic acid, phosphoric acid, sulphuric acid, nitric acid, and organic acids such as p-toluensulphonic or metansulphonic acid.

The new derivatives of general formula (I) can be prepared by the methods A-G indicated below:

Method A:

Compounds with the general formula (I) can be obtained by reaction of the amine with general formula (II), in which $R_1$ is as described above with a carboxylic acid with general formula $R_2COOH$ (III), in which $R_2$ has the above described meaning, or with a salt of this acid or a reaction derivative $R_2COX$ (IV), (Diagram 1).

Diagram 1

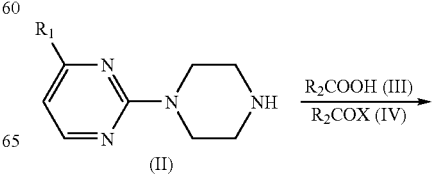

-continued

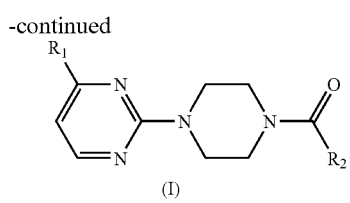

Examples of these salts include salts of alkali metals, such as sodium and potassium salts, alkaline-earth metals such as calcium and magnesium salts, ammonium salt and salts of organic bases such as triethylamine, trimethylamine, pyridine and picoline.

Examples of reaction derivatives with the general formula $R_2COX$ (IV) include those in which X is a halogen atom, preferably a chlorine or bromine atom, an azide group ($—N_3$), a 1-imidazolyl group, an $OR—CO—R_4$ group, where $R_4$ can be an alkyl radical with 1 to 6 carbon atoms or an aryl, optionally substituted with one or more halogen atoms, or an $OR_5$ group, where $R_5$ represents an aromatic group with one or two rings, substituted with one or more halogen atoms or nitro radicals, preferably with the groups 4-nitrophenyl, 2,4-dinitrophenyl, pentachlorophenyl, pentafluorophenyl, 1-benzotriazolyl or N-succinimide. Likewise, instead of using the aforementioned reaction derivatives the compounds with the general formula (I) can be prepared directly by reaction of the amine (II) with a carboxylic acid with the general formula $R_2COOH$ (III), in which case it is preferable to have the reaction occur in the presence of carbonyl group activation reagents, such as N,N'-dicyclohexylcarbodiimide, N,N'-diisopropylcarbodiimide or 3-(3-dimethylamino)propyl-1-ethylcarbodiimide. This reaction can also take place using the aforementioned carbodiimides in the presence of 1-benzotriazol or N-hydroxisuccinimide. Acids with the general formula (III) and the amine with the general formula (II) also react directly in the presence of N,N'-carbonyldiimidazol or of the anhydride of propanophosphonic acid.

The reaction occurs in an organic solvent as an organic chlorinated hydrocarbon, such as dichloromethane or chloroform, a linear or cyclic ether such as 1.2-dimethoxyethane, tetrahydrophurane or dioxane, a polar aprotic solvent such as pyridine, dimethylsulphoxide, acetonitryl or dimethylformamide, or any other suitable solvent. The reaction may occur in the presence of a mineral or organic base, such as an aliphatic amine, preferably triethylamine or N-methylmorpholine and is stirred at a temperature between ambient temperature and the boiling point of the solvent for a period between ten minutes and twenty-four hours, with the preferred conditions being between thirty minutes and five hours.

Method B:

The new derivatives with the general formula (I), where $R_1$ is as described above and $R_2$ represents a cyanoaryl radical, can be prepared according to the method shown in Diagram 2:

Reaction of the amine with the general formula (II), where $R_1$ is as described above, with 3-bromophthalide (V) provides the aldehyde with the general formula (VI), where $R_1$ is as described above (Alonso, R., Castedo, L., Dominguez, D., J. Org. Chem. 1989.54 (2), 424).

The reaction takes place in an organic solvent as an organic chlorinated hydrocarbon, such as dichloromethane or chloroform, a linear or cyclic ether such as 1,2-dimethoxyethane, tetrahydrophurane or dioxane, a polar aprotic solvent such as pyridine, dimethylsulphoxide, acetonitryl or dimethylformamide, or any other suitable solvent. The reaction may occur in the presence of a mineral or organic base, such as an aliphatic amine, preferably triethylamine or N-methylmorpholine and is stirred at a temperature between ambient temperature and the boiling point of the solvent for a period between ten minutes and twenty-four hours, with the preferred conditions being between thirty minutes and five hours.

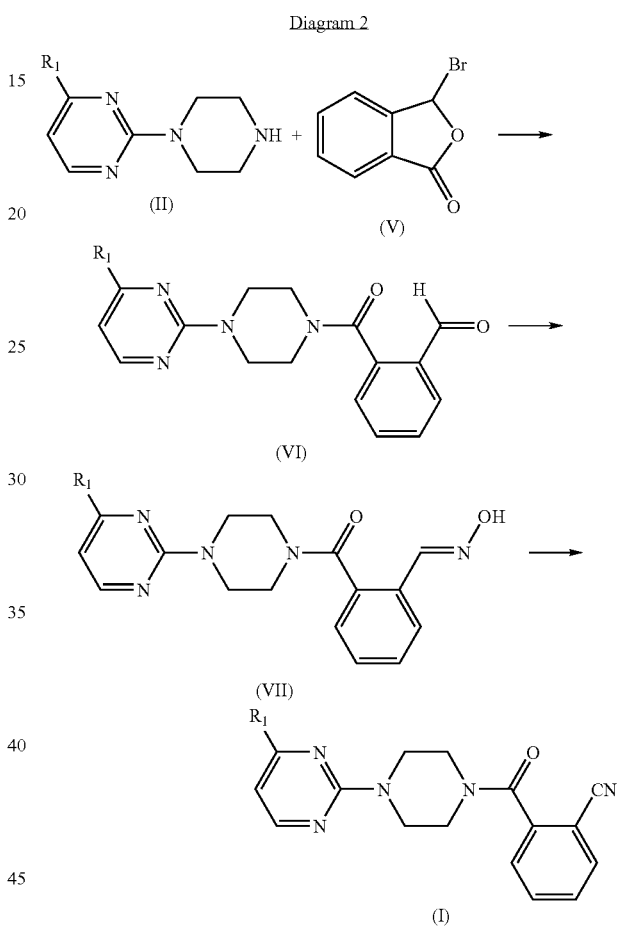

Diagram 2

The oxime with general formula (VII) in which $R_1$ is as described above is obtained by the reaction of the aldehyde with general formula (VI) with hydroxylamine or a hydroxylamine salt. The reaction takes place in an organic solvent such as ethanol, or a mixture of ethanol and water or any other suitable solvent. The reaction occurs in the presence of a base such as sodium hydroxide, sodium carbonate of sodium acetate, or an aliphatic amine, preferably pyridine, triethylamine or N-methylmorfoline and is stirred at a temperature between the ambient temperature and the boiling point of the solvent for a period between one hour and twenty-four hours.

The transformation of the oxime with the general formula (VII), in which $R_1$ is as described above, into the derived cyan with general formula (I) where $R_1$ is as described above is obtained by the reaction of the oxime (VII) with several dehydration reagents, such as $(PhO)_2PHO$, $p-ClC_6H_4OC(=S)Cl$, N,N'-carbonyldiimidazol, as well as in the presence of Cu(II) ions such as $Cu(AcO)_2$, or by acylation of the aldoxime acetic anhydride or trifluouroacetic anhydride and later formation of the cyano radical with bases such as sodium hydroxide, potassium hydroxide, sodium carbonate, potassium carbonate, pyridine or triethylamine. The reaction takes place at a temperature between ambient temperature and the boiling point of the solvent for a period between one hour and 4 days.

Method C:

The new derivatives with the general formula (I), where $R_1$ is as described above and $R_2$ represents a cyanoaryl or cyanopyridyl radical can be prepared according to the method represented in Diagram 3:

twenty-four hours, with the preferred conditions being between thirty minutes and five hours.

Reaction of the acid with general formula (IX) takes place in the presence of carbonyl group activation reagents such as N,N'-dicyclohexycarbodiimide, N,N'-diisopropylcarbodiimide or 3-(3-dimethylamino)propyl-1-ethylcarbodiimide. This reaction can also occur using said carbodiimides in the presence of 1-benzotriazol or N-hydroxisuccinimide or by reaction of the acid (IX) with reagents such as thyonil chloride, oxalyl chloride, ethyl chloroformiate, pivaloyl chloroformiate or methansulfonyl chloride. The acid with the general formula (IX) and the amine with the general

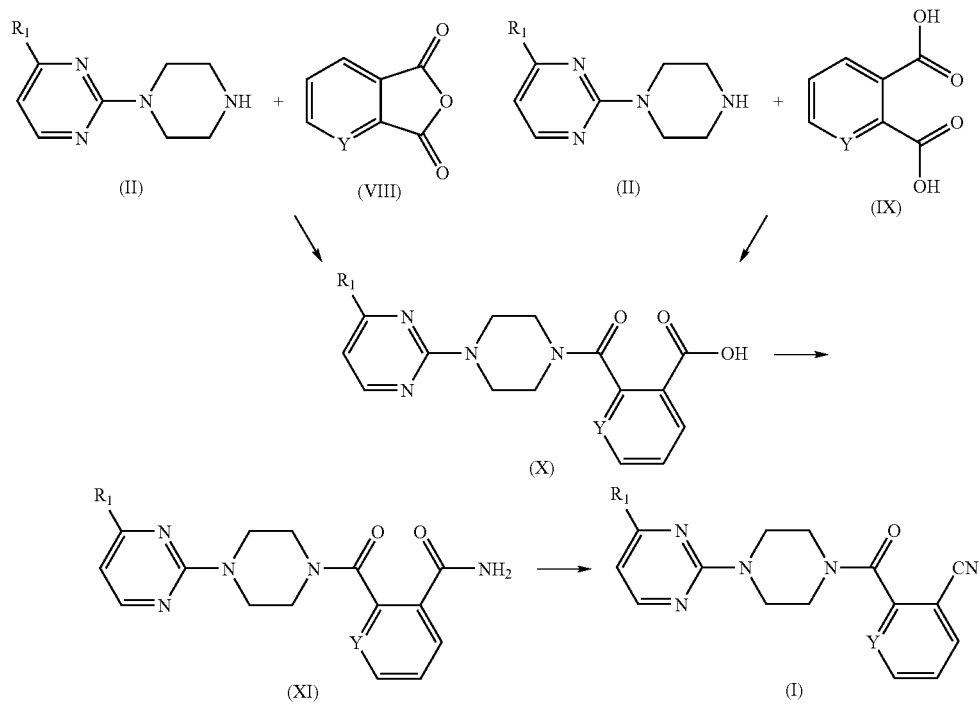

Diagram 3

Reaction of the amine with general formula (II), in which $R_1$ is as described above, with an anhydride with the general formula (VIII) where Y represents a nitrogen atom (N) or an aromatic carbon atom joined to a hydrogen atom (CH), or reaction of the amine with the general formula (II), in which $R_1$ is as described above, with an acid with the general formula (IX) where Y represents a nitrogen atom (N) or an aromatic carbon atom joined to a hydrogen atom (CH) produces the acid with the general formula (X) where $R_1$ and Y are as described above.

Reaction with the anhydride (VIII) takes place in an organic solvent as an organic chlorinated hydrocarbon, such as dichloromethane or chloroform, a linear or cyclic ether such as 1,2-dimethoxyethane, tetrahydrophurane or dioxane, a polar aprotic solvent such as pyridine, dimethylsulphoxide, acetonitryl or dimethylformamide, or any other suitable solvent. The reaction may occur in the presence of a mineral or organic base, such as an aliphatic amine, preferably triethylamine or N-methylmorpholine and is stirred at a temperature between ambient temperature and the boiling point of the solvent for a period between ten minutes and formula (II) also react directly in the presence of N,N'-carbonyldiimidazol or the anhydride of propanophosphonic acid. The reaction occurs in an organic solvent such as methylene chloride, chloroform, pyridine or any other suitable solvent. The reaction occurs in the presence of a base such as sodium hydroxide, sodium carbonate or sodium acetate or an aliphatic amine, preferably pyridine, triethylamine or N-methylmorfoline and is stirred at a temperature between the ambient temperature and the boiling point of the solvent for a period between one hour and twenty-four hours.

The amide with the general formula (XI), in which $R_1$ and Y are as indicated above, is obtained by reacting the acid with the general formula (X) with carbonyl group activation reagents and later treatment with ammonia. Activation of the carbonyl group of the acid with the general formula (X) is obtained by reacting (X) with reactants such as thionyl chloride, oxalyl chloride, ethyl chloroformiate, pivaloyl chloroformiate or methansulfonyl chloride. Reaction of the acid (X) with ammonia can also take place in the presence of carbonyl group activation reagents such as N,N'-dicyclohexylcarbodiimide, N,N'-diisopropylcarbodiimide or 3-(3-dimethylamino)propyl-1-ethylcarbodiimide. This reaction can also occur using the aforementioned carbodiimides in the presence of 1-benzotriazol or N-hydroxisuccinimide. The acid with the general formula (X) and the ammonia also react directly in the presence of N,N'-carbonyldiimidazol. The reaction occurs in an organic solvent such as methylene chloride, chloroform, pyridine or any other suitable solvent. The reaction occurs in the presence of a base such as sodium hydroxide, sodium carbonate or sodium acetate, an aliphatic amine, preferably pyridine, triethylamine or N-methylmorpholine and is stirred at a temperature between ambient temperature and the boiling point of the solvent for a period between one and twenty-four hours.

Transformation of the amide with the general formula (XI), in which $R_1$ and Y are as described above, into the cyano derivative with the general formula (I) where $R_1$ and Y are as described above is achieved by dehydration of the amide (XI) with several reagents, such as thionyl chloride, oxalyl chloride, trifluoroacetic anhydride, catalytic $Bu_2SnO$ or preferably methansulfonyl chloride (A. D. Dunn, M. J. Mills and W. Henry, Org. Prep. Proced. Int., 1982 Vol. 14(6) 396-399) or other dehydration reagents. The reaction occurs in an organic solvent such as dimethylformamide, methylene chloride, toluene and in the presence of a base such as triethylamine or pyridine at a temperature between 0° C. and the boiling point of the solvent for a period between one hour and twenty-four hours.

Method D:

The new derivatives with the general formula (I), where R1 is as described above and $R_2$ represents a cyanoaryl or cyanopyridyl radical can be prepared according to the method represented in Diagram 4.

By reaction of the amine with with the general formula (II), in which R1 is as described above, with a carboxylic acid with the general formula (XII), where $R_6$ represents an alkyl radical such as methyl or ethyl and Y represents a nitrogen atom (N) or an aromatic carbon atom joined to a hydrogen atom (CH), the amide is obtained with the general formula (XIII) where $R_1$. $R_6$ and Y are as described above.

The reaction takes place by treating the acid with general formula (XII) with activation reactants for the carbonyl group and later treatment with the amine with the general formula (II). Activation of the carbonyl group of the acid with the general formula (XII) is achieved by treatment with reagents such as thionyl chloride, oxalyl chloride, ethyl chloroformiate, pivaloyl chloroformiate or methansulphonyl chloride. Reaction of the acid (XII) and the amine with the general formula (II) can also occur in the presence of carbonyl group activation reagents such as N,N'-dicyclohexylcarbodiimide, N,N'-diisopropylcarbodiimide or 3-(3-dimethylamino)propyl-1-ethylcarbodiimide. This reaction can also be effected with the aforementioned carbodiimides in the presence of 1-benzotriazol or N-hydroxisuccinimide. The acid with the general formula (XII) and the amine (II) also react directly in the presence of N,N'-carbonyldiimidazol or of the anhydride of propanophosphonic acid. The reaction takes place in an organic solvent such as methylene chloride, chloroform, pyrimidine or any other suitable solvent. The reaction occurs in the presence of a base such as sodium hydroxide, sodium carbonate, sodium acetate or an aliphatic amine, preferably pyrimidine, triethylamine or N-methylmorpholin and is stirred at a temperature between the ambient temperature and the boiling point of the solvent for a period between one hour and twenty-four hours.

Hydrolysis of the ester group of the amide with the general formula (XIII), in which $R_1$, $R_6$ and Y are as described above leads to formation of the acid with the general formula (XIV) where $R_1$ and Y are as described above. Hydrolysis is achieved by conventional methods, such as saponification with sodium hydroxide, potassium hydroxide, lithium hydroxide, sodium carbonate or potassium carbonate or by hydrolysis in an acid medium, such as hydrochloric acid. The reaction occurs in a solvent such as methanol, ethanol, water, tetrahydrofurane or in a mixture of these at a temperature between ambient temperature and the boiling point of the solution for a period between one hour and twenty-four hours.

The amide with the general formula (XV) in which $R_1$ and Y are as described above is obtained by reaction of the acid with the general formula (XIV) with carbonyl group activation reactants and later treatment with ammonia. Activation of the carbonyl group of the acid with the general formula (XIV) is achieved by reagents such as thionyl chloride, oxalyl chloride, ethyl chloroformiate, pivaloyl chloroformiate or methansulphonyl chloride. Reaction of the acid (XIV) with ammonia can also occur in the presence of carbonyl group activation reactants such as N,N'-dicyclohexylcarbodiimide, N,N'-diisopropylcarbodiimide or 3-(3-dimethylamino)propyl-1-ethylcarbodiimide. This reaction can also take place with the aforementioned carbodiimides in the presence of 1-benzotriazol or N-hydroxysuccinimide. The acid with the general formula (XIV) and ammonia also react directly in the presence of N,N'-carbonyldiimidazol. The reaction occurs in an organic solvent such as methylene chloride, chloroform or pyridine, or any other suitable solvent. The reaction occurs in the presence of a base such as sodium hydroxide, sodium carbonate, sodium acetate or an aliphatic amine, preferably pyridine, triethylamine or N-methylmorfoline and is stirred at a temperature between the ambient temperature and the boiling point of the solvent for a period between one hour and twenty-four hours.

Diagram 4

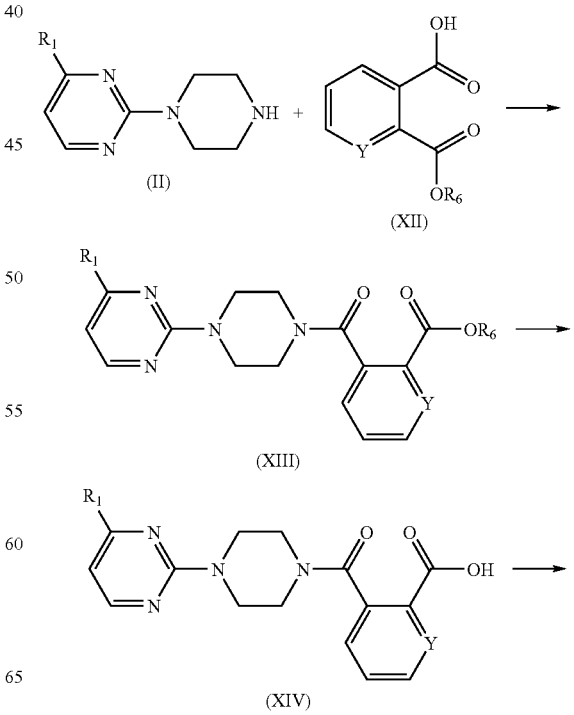

-continued

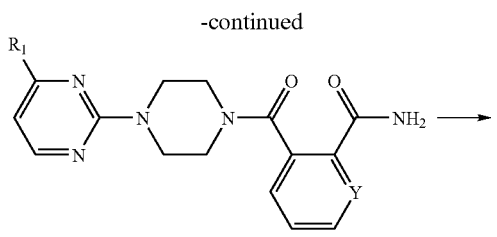

(XV)

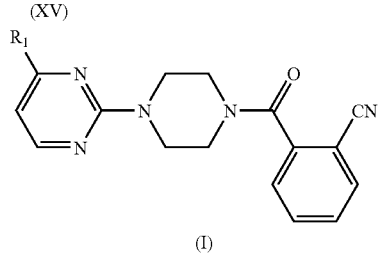

(I)

Transformation of the amide with the general formula (XV), in which $R_1$ and Y are as described above, into the cyano derivate with the general formula (I), where $R_1$ and Y are as described above, is achieved by dehydration of the amide (XV) by several reagents such as thionyl chloride, oxalyl chloride, trifluoroacetic anhydride, catalytic $Bu_2SnO$ or preferably methansulfonyl chloride (A. D. Dunn, M. J. Mills and W. Henry, Org. Prep. Proced. Int., 1982 Vol. 14(6) 396-399) or other dehydration reactants. The reaction takes place in an organic solvent such as DMF, methylene chloride or toluene and in the presence of a base such as triethylamine or pyridine at a temperature between 0° C. and the boiling point of the solvent for a period between one hour and twenty-four hours.

Method E:

The new derivatives with the general formula (I), where R1 is as described above and $R_2$ represents cyanothienyl or cyanofuryl radical can be prepared by the method represented in Diagram 5:

Diagram 5

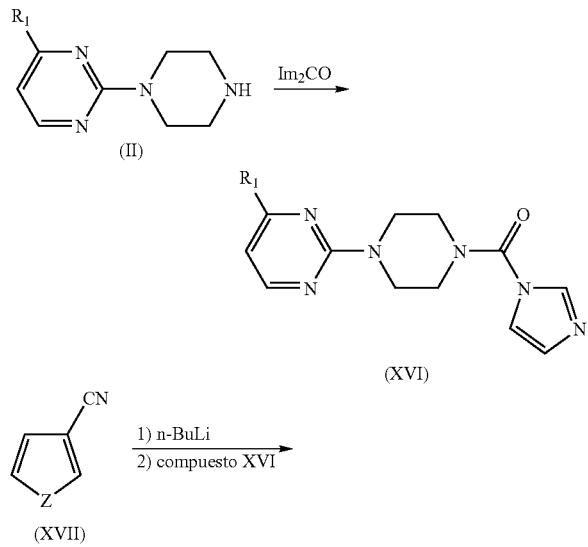

-continued

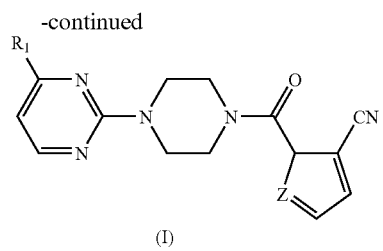

(I)

Reaction of the amine with the general formula (II), in which R1 is as described above, with N,N'-carbonyldiimidazol gives the compound with the general formula (XVI). The reaction takes place in an anhydrous organic solvent, such as tetrahydrofurane or dimethylformamide, at a temperature ranging between 0° C. and ambient temperature for a time between one and twenty-four hours.

Metallation of a compound with the general formula (XVII) where Z stands for a sulphur atom (S) or an oxygen atom (OR) with n-BuLi, sec-BuLi or tert-BuLi in an anhydrous solvent such as tetrahydrofurane at a temperature of −78° C. and later addition of the compound (XVI) gives the derivative cyano with the general formula (I), where $R_1$ and Z are as described above.

Method F:

The new derivatives with general formula (I), where $R_1$ and $R_2$ are as described above, can be obtained by reaction of the chloropyrimidine derivative with the general formula (XVIII), where $R_1$ is as described above, with a piperazine derivative with the general formula (XIX), where $R_2$ is as described above, according to the method represented in Diagram 6:

Diagram 6

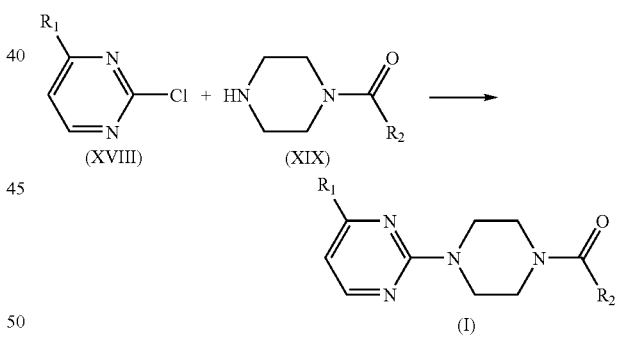

The reaction takes place in an organic solvent, such as a chlorinated organic hydrocarbon as dichloromethane or chloroform, a linear or cyclic ether such as 1,2-dimethoxyethane, tetrahydrofurane or dioxane, an aprotic polar solvent such as pyridine, dimethylsulphoxide, dimethylformamide or acetonitryl, a protic polar solvent such as methanol, ethanol, isopropanol or n-butanol or any other suitable solvent for effecting an aromatic nucleophilic substitution reaction. The reaction may take place in the presence of a mineral base such as sodium carbonate or potassium carbonate, or an organic one such as an aliphatic amine, preferably triethylamine or N-methylmorfoline and is stirred at a temperature between the ambient temperature and the boiling point of the solvent for a period ranging between ten minutes and twenty-four hours, with the period between thirty minutes and five hours being the preferred conditions.

Method G:

Salts of compounds with the general formula (I) are prepared by reaction with a mineral acid such as hydrochloric acid, hydrobromic acid, phosphoric acid, sulphuric acid, nitric acid or with an organic acid such as p-toluensulphinic acid or methansulphonic acid in a suitable solvent, such as methanol, ethanol, ethylic ether, ethyl acetate or acetone, with the corresponding salts obtained by the conventional precipitation or crystallisation techniques.

The carboxylic acid used in the preparation of the cyano derivatives with the general formula (I), where $R_1$ and $R_2$ are as described above, according to the methods described in the present invention are commercially available or have been prepared by several procedures described in the scientific literature (Kenneth A. Hold and Phillip Shadbolt, Br. Polym. J., 1983. 15 (4), 201-207; Carol K. Sauers and Robert J. Cotter, J. Org. Chem., 1961. 26. 6-10; Louis A. Carpino, J. Am. Chem. Soc., 1962. 84. 2196-2201; A. D. Dunn, M. J. Mills and W. Henry, Org. Prep. Proced. Int., 1982. 14(6), 396-399; Pierre Dubus, Bernard Decroix, Jean Morel et Paul Pastour, Bull. Soc. Chim. Fr., 1976. (3-4. Pt. 2), 628-634; William M. Murray and J. Edward Semple, Synthesis, 1996. 1180-1182; Luc I. M. Spiessens and Marc J. OR. Anteunis, Bull. Soc. Chim. Belg., 1980. 89 (3), 205-231; I. Thunus et M. Dejardin-Duchéne, J. Pharm. Belg., 1969. 51. 3-21; S. Fallab und H. Erlenmeyer, Helv. Chim. Acta, 1951. 34. 488-496).

The following examples describe the preparation of new compounds in accordance with the invention. Also described are some typical uses in the various fields of application, as well as gallenical formulae applicable to the compounds object of the invention.

The methods described below are provided for purposes of illustration only and should not be taken as a definition of the limits of the invention.

Method A:

EXAMPLE 1

Preparation of 2-[4-(2-cyanobenzoyl)-1-piperazinyl]-4-methoxypyrimidine

To a suspension of 2.0 g (14 mmol) of 2-cyanobenzoic acid in 100 mL of $CH_2Cl_2$ are added 1.5 mL (17.5 mmol) of oxalyl chloride and a catalytic amount of pyridine. The suspension is left stirred at room temperature for 3 hours. The solvent is evaporated at reduced pressure, giving a crude which is suspended in 100 mL of $CH_2Cl_2$ and which is slowly added on a solution of 2.45 g (12.6 mmol) of 4-methoxy-2-(1-piperazinyl)pyrimidine and 4 mL (28 mmol) of triethylamine in 50 mL of $CH_2Cl_2$ cooled to 0° C. in an ice bath. The solution is kept at 0° C. for one hour and is allowed to reach room temperature. The reaction mixture is washed with $H_2O$, dried with $Na_2SO_4$ and the solvent eliminated at reduced pressure. The resulting crude is purified by chromatography on silica gel, using ethyl acetate as eluent, providing 2.06 g (6.4 mmol) of 2-[4-(2-cyanobenzoyl)-1-piperazinyl]-4-methoxipyrimidine with m.p.=166-168° C.

Method B:

EXAMPLE 3

Preparation of 2-[4-(2-cyanobenzoyl)-1-piperazinyl]-4-ethoxypyrimidine

To a solution of 2.08 g (10 mmol) of 4-ethoxy-2-(1-piperazinyl)pyrimidine and 5 mL of triethylamine in 60 mL of dry THF are added 2.15 g (10 mmol) of 3-bromophthalida and kept stirred at room temperature for 4 hour. The triethylamine hydrobromide is filtered and washed with THF, and the solvent eliminated at reduced pressure, providing a crude which is purified by chromatography on silica gel, using ethyl acetate as eluent, yielding 2.45 g (7.20 mmol) of 4-ethoxy-2-[4-(2-formylbenzoyl)-1-piperazinyl]pyrimidine with m.p.=134-136° C.

To a solution of 2.45 g (7.2 mmol) of 4-ethoxy-2-[4-(2-formilbenzoyl)-1-piperazinyl]pyrimidine in ethanol —$H_2O$ (80:20) are added 2.5 g (18.4 mmol) of AcONax3$H_2O$ and 0.75 g (8.6 mmol) of hydroxylamine hydrochloride. The reaction mixture is taken to reflux and its evolution monitored by TLC. The solvent is eliminated at reduced pressure, diluted in $CH_2Cl_2$ and washed with $H_2O$. The organic solvent is evaporated at reduced pressure, giving an oil which is crystallised of ethyl ether, yielding 0.5 g (1.40 mmol) of 4-ethoxy-2-{4-[2-(hidroxyaminomethyl)benzoyl]-1-piperazinyl}pyrimidine with m.p.=136-140° C.

To a solution of 0.5 g (1.40 mmol) of 4-ethoxy-2-{4-[2-(hidroxyaminomethyl)benzoyl]-1-piperazinyl}pyrimidine in 30 mL of ethyl acetate are added 0.15 mL of acetic anhydride and filled to in reflux for 2 hours. The solvent is evaporated under reduced pressure providing the acetylated oxime.

The acetylated oxime is dissolved in 20 mL of acetonitryl and added the excess $K_2CO_3$ and left stirring at ambient temperature for 78 hours. The solid is filtered, the solvent eliminated at reduced pressure, diluted in $CH_2Cl_2$ and washed with $H_2O$. The solvent is evaporated at reduced pressure, giving a crude which crystallises in ethyl ether, yielding 0.2 g (0.60 mmol) of 2-[4-(2-cyanobenzoyl)-1-piperazinyl]-4-ethoxypyrimidine with m.p.=151-154° C.

Method C:

EXAMPLE 15

Preparation of 2-[4-(3-cyano-2-pyridilcarbonyl)-1-piperazinyl]-4-ethoxypyrimidine To a suspension of 0.75 g (5.04 mmol) of quinilinic anhydride in 25 mL of acetonitryl are added 1.05 g (5.04 mmol) of 4-ethoxy-2-(1-piperazinyl)pyrimidine and 0.8 mL (5.07 mmol) of triethylamine and taken to reflux for 18 hours. The solvent is evaporated at reduced pressure and the resulting crude is purified by chromatography on silica gel, using as eluents $CHCl_3$:MeOH 3:2 obtaining 0.6 g (1.68 mmol) of 2-[4-(3-carboxy-2-pyridilcarbonyl)-1-piperazinyl]-4-ethoxypyrimidine with m.p.=186-189° C.

To a suspension of 0.3 g (0.8 mmol) of 2-[4-(3-carboxy-2-pyridilcarbonyl)-1-piperazinyl]-4-ethoxypyrimidine in 20 mL of methylene chloride are added 0.5 mL (3.6 mmol) of triethylamine, taken to 0° C. and added 0.1 g (0.92 mmol) of ethyl chloroformate keeping the solution at this temperature for 30 minutes. Through the resulting mixture is bubbled $NH_3$ (gas) for 1 minute and the temperature kept at 0° C. for 2 hours. The solution is allowed to reach ambient temperature and washed with $H_2O$, the methylene chloride is eliminated at reduced pressure obtaining a paste which solidifies yielding 184 mg (0.51 mmol) of 2-[4-(3-carbamoil-2-pyridilcarbonyl)-1-piperazinyl]-4-ethoxypyrimidine with m.p.=161-163° C.

To a solution of 84 mg (0.23 mmol) of 2-[4-(3-carbamoyl-2-pyridilcarbonyl)-1-piperazinyl]-4-ethoxypyrimidine in 15 mL of methylene chloride are added 0.2 mL of triethylamine and 0.1 mL of methansulfonyl chloride. The resulting mixture is left stirring for 18 hours at ambient temperature. The organic solution is washed with a solution of $CO_3Na_2$, the solvent eliminated at reduced pressure obtaining a crude which is purified by chromatography on silica gel, using ethyl acetate as an eluent yielding 42 mg (0.12 mmol) of 2-[4-(3-cyano-2-pyridilcarbonyl)-1-piperazinyl]-4-ethoxypyrimidine with m.p.=137-140° C.

Method D:

EXAMPLE 19

Preparation of 2-[4-(2-cyano-3-pyridilcarbonyl)-1-piperazinyl]-4-ethoxypyrimidine To a solution of 1.33 g (7.45 mmol) of 2-methoxycarbonyinicotinic acid in 15 mL of DMF cooled in an ice bath are added 1.20 g (7.45 mmol) of N,N'-carbonyldiimidazol and stirred for 40 minutes. To the reaction mixture is added 1.53 g (7.45 mmol) of 4-ethoxy-2-(1-piperazinyl)pyrimidine and left at ambient temperature for two hours. The solution is then diluted with ethyl acetate and washed with $H_2O$, dried with $Na_2SO_4$ and the solvent eliminated at reduced pressure, obtaining an oil which crystallises as ethyl ether, yielding 1.5 g (4.04 mmol) of 4-ethoxy-2-[4-(2-methoxycarbonyl-3-pyridilcarbonyl)-1-piperazinyl]pyrimidine with m.p.=126-128° C.

To a solution of 1.4 g (3.77 mmol) of 4-ethoxy-2-[4-(2-methoxycarbonyl-3-pyridilcarbonyl)-1-piperazinyl]pyrimidine in 25 mL of THF and 10 mL of MeOH are added 0.158 g (3.77 mmol) of $LiOHxH_2O$ and left stirred at ambient temperature for two hours. Through the solution is bubbled $SO_2$ and the solvent is eliminated at reduced pressure. The resulting crude is suspended in 30 mL of methylene chloride and 0.45 mL (3.3 mmol) of triethylamine added, and it is taken to 0° C. and 0.3 g (2.76 mmol) of ethyl chloroformiate are added, keeping the solution at this temperature for 30 minutes. Through the resulting mixture is bubbled $NH_3$ (gas) for 1 minute and the temperature kept at 0° C. for 2 hours. The solution is allowed to reach ambient temperature and washed with $H_2O$. The methylene chloride is eliminated at reduced pressure, and a paste is obtained which solidifies to a crude which crystallises as ethyl acetate, yielding 0.12 g (0.34 mmol) of 2-[4-(2-carbarnoil-3-pyridilcarbonyl)-1-piperazinyl]-4-ethoxypyrimidine with m.p.=152-156° C.

To a solution of 100 mg (0.28 mmol) of 2-[4-(2-carbamoil-3-pyridilcarbonyl)-1-piperazinyl]-4-ethoxypyrimidine in 5 mL of pyridine are added 1.0 mL of methansulphonyl chloride. The resulting mixture is stirred for 24 hours at ambient temperature. The solvent is evaporated to dryness and distributed in methylene chloride and water, washed with $NaHCO_3$ and the solvent eliminated at reduced pressure, providing a crude which is purified by chromatography on silica gel using as eluent ethyl acetate, yielding 60 mg (0.18 mmol) of 2-[4-(2-cyano-3-pyridilcarbonyl)-1-piperazinyl]-4-ethoxypyrimidine with m.p.=177-178° C.

Method E:

EXAMPLE 9

Preparation of 2-[4-(3-cyano-2-tienilcarbonyl)-1-piperazinyl]-4-methoxypyrimidine To a solution of 1.5 g (7.7 mmol) of 4-methoxy-2-(1-piperazinyl)pyrimidine in 20 mL of THF cooled to 0° C. are added 1.25 g (7.7 mmol) of N,N'-carbonyldiimidazol. The mixture is left stirring at ambient temperature for 3 hours. The solvent is eliminated at reduced pressure and $H_2O$ is added, forming a precipitate which is filtered to obtain 1.8 g (6.24 mmol) of 2-[4-(1-imidazolilcarbonyl)-1-piperazinyl]-4-methoxypyrimidine with m.p.=125-126° C.

To a solution of 0.62 mL (6.8 mmol) of 3-cyanothiofene in 25 mL of anhydrous THF cooled to −78° C. and in an argon atmosphere are slowly added 4.26 mL (6.8 mmol) of n-BuLi 1.6M in hexane. The mixture is kept at −78° C. during 30 minutes and later is slowly added a solution of 1.8 g (6.2 mmol) of 2-[4-(1-imidazolilcarbonyl)-1-piperazinyl]-4-methoxypyrimidine in 25 mL of anhydrous THF. The mixture is allowed to slowly reach ambient temperature and it is kept at this temperature for 2 hours. The solution is poured over water and extracted with ethyl acetate, producing a crude which is purified by chromatography over silica gel using as eluent a mixture of ethyl acetate:hexane 7:3, yielding 1.0 g (3.0 mmol) of 2-[4-(3-cyano-2-tienilcarbonyl)-1-piperazinyl]-4-methoxypyrimidine with m.p.=140-142° C.

Method F:

EXAMPLE 1

Preparation of 2-[4-(2-cyanobenzoyl)-1-piperazinyl]-4-methoxypyrimidine

To a solution of 1.0 g (6.8 mmol) of 2-cyanobenzoic acid in 20 mL of anhydrous DMF cooled to 0° C. are added 1.1 g (6.8 mmol) of N,N'-carbonyldiimidazol and kept stirred for 40 minutes. Later are added 1.26 g (6.8 mmol) of 1-(tert-butoxicarbonyl)piperazine and left at ambient temperature for 2 hours. It is poured on water and extracted with ethyl ether. The organic phase is dried and evaporated at reduced pressure, giving a crude which solidifies as petroleum ether to yield 1.24 g (3.94 mmol) of 4-(tert-butoxicarbonyl)-1-(2-cyanobenzoyl)piperazine with m.p.=126-128° C.

To a solution of 1.2 g (3.81 mmol) of 4-(tert-butoxicarbonyl)-1-(2-cyanobenzoyl)piperazine in 10 mL of methylene chloride cooled to 0° C. are added 10 mL of trifluoroacetic acid and left stirred at room temperature for 2 hours. The reaction mixture is evaporated to dryness and the resulting crude crystallises in methylene chloride: ethyl ether, yielding 1.04 g (3.16 mmol) of 1-(2-cyanobenzoyl) piperazine trifluoroacetate with m.p.=136-141° C.

A mixture of 1.0 g (3.04 mmol) of 1-(2-cyanobenzoyl) piperazine trifluoroacetate, 0.5 g (3.35 mmol) of 2-chloro-4-methoxypyrimidine and 1.0 g (6.68 mmol) of potassium carbonate in 20 mL of DMF is heated to 100° C. for 1 hour. The solvent is eliminated at reduced pressure and water is added. The resulting solid is filtered, washed with water and purified by chromatography over silica gel, using as eluent ethyl acetate, yielding 0.51 g (1.58 mmol) of 2-[4-(2-cyanobenzoyl)-1-piperazinyl]-4-methoxypyrimidine.

Method G:

EXAMPLE 4

Preparation of 2-[4-(2-cyanobenzoyl)-1-piperazinyl]-4-ethoxypyrimidine hydrochloride.

4.76 g (14.12 mmol) of 2-[4-(2-cyanobenzoyl)-1-piperazinyl]-4-ethoxypyrimidine are dissolved in acetone and a few drops of ethyl ether/HCl and ethyl ether are added, forming a precipitate which is filtered and dried, providing 3.85 g (10.31 mmol) of 2-[4-(2-cyanobenzoyl)-1-piperazinyl]-4-ethoxypyrimidine hydrochloride with m.p.=147-151° C.

In Table 1 a few compounds which are illustrative of the invention are described, indicating their method of obtention, melting point and spectroscopic characteristics.

TABLE I

| Example | R₁ | R₂ | Base or salt | METHOD | m.p. (° C.) | ¹H RMN (MHz) (Solvent) δ | IR, cm⁻¹ |
|---|---|---|---|---|---|---|---|
| 1 | $CH_3O-$ | 2-cyanophenyl | Base | A, B or F | 166-168 | (300 MHz) (CDCl₃) 3.35(m, 2H)3.78-4.02 (a.c., 9H, (δ=3.85.s)), 6.01(d, J=5.7Hz, 1H), 7.50(m, 2H), 7.66(t, J=7.5 Hz, 1H), 7.72(d, J=7.5Hz, 1H), 8.03(d, J=5.7 Hz, 1H). | (KBr) 2226. 1632. 1598. 1565. 1431. 1259. 987. |
| 2 | $CH_3O-$ | 2-cyanophenyl | HCl | G | 154-156 | (300 MHz) (CDCl₃) 3.52(broad band, 2H), 3.85-4.38(a.c., 9H, (δ=4.05.s)), 6.28(d, J=6.8Hz, 1H), 7.46(d, J=7.6Hz, 1H), 7.56(t, J=7.6Hz, 1H), 7.71(m, 2H), 8.70 (d, J=6.8Hz, 1H). | (KBr) 3700-2300 (broad band), 2228. 1644. 1609. 1485. 1257. |
| 3 | $CH_3CH_2O-$ | 2-cyanophenyl | Base | A, B or F | 151-154 | (300 MHz) (CDCl₃) 1.34(t, J=7.1Hz, 3H), 3.34(m, 2H), 3.77-3.99(a.c., 6H), 4.29(q, J=7.1Hz, 2H), 5.99(d, J=5.8Hz, 1H), 7.50(m, 2H), 7.66(t, J=7.7Hz, 1H), 7.72 (m, 1H), 8.03(d, J=5.8Hz, 1H). | (KBr) 2220. 1632. 1560. 1491. 1432. 1256. 1002. |
| 4 | $CH_3CH_2O-$ | 2-cyanophenyl | HCl | G | 147-151 | (300 MHz) (CDCl₃) 1.43(t, J=7.3Hz, 3H), 3.52(broad band, 2H), 3.85-4.35(a.c., 6H), 4.48(q, J=7.3Hz, 2H), 6.25(d, J= 6.7Hz, 1H), 7.46(d, J=8.0Hz, 1H), 7.56 (t, J=8.0Hz, 1H), 7.70(m, 2H), 8.06(d, J=6.7Hz, 1H). | (KBr) 3700-2300 (broad band), 2228. 1638. 1605. 1481. 1433. 1254. |
| 5 | $CH_3[CH_2]_2O-$ | 2-cyanophenyl | Base | A, B or F | 118-121 | (300 MHz) (CDCl₃) 0.97(t, J=7.4Hz, 3H), 1.73(m, 2H), 3.34(broad band, 2H), 3.77-3.98(a.c., 6H), 4.18(t, J=6.7Hz, 2H), 6.00(d, J=5.7Hz, 1H), 7.50(m, 2H), 7.66 (t, J=8.0Hz, 1H), 7.71(d, J=8.0Hz, 1H), 8.02(d, J=6.7Hz, 1H). | (KBr) 2220. 1629. 1586. 1559. 1428. 1240. 1005. |
| 6 | $CH_3[CH_2]_2O-$ | 2-cyanophenyl | HCl | G | 147-149 | (300 MHz) (CDCl₃) 1.02(t, J=7.0Hz, 3H), 1.82(m, 2H), 3.52(broad band, 2H), 3.84-4.17(a.c., 4H), 4.36(m, 4H), 6.27(d, J= 6.6Hz, 1H), 7.45(d, J=7.4Hz, 1H), 7.56 (t, J=7.5Hz, 1H), 7.70(m, 2H), 8.05(d, J=6.6Hz, 1H). | (KBr) 3300-2300 (broad band), 2235. 1647. 1601, 1485. 1452. 1283. 1261. |
| 7 | $CH_3[CH_2]_3O-$ | 2-cyanophenyl | Base | A, B or F | 71-73 | (300 MHz) (CDCl₃) 0.93(t, J=7.3Hz, 3H), 1.42(m, 2H), 1.69(m, 2H), 3.35(broad singlet, 2H), 3.75-4.00(a.c., 6H), 4.23(t, J=6.5Hz, 2H), 5.99(d, J=5.7Hz, 1H), 7.50(m, 2H), 7.66(dt, J=7.7Hz, J'=1.0 Hz, 1H), 7.72(d, J=7.7Hz, 1H), 8.02(d, J=5.7Hz, 1H). | (KBr) 2966. 2225. 1632. 1561. 1500. 1464. 1240. 1006. |
| 8 | $CH_3[CH_2]_3O-$ | 2-cyanophenyl | HCl | G | 137-138 | (300 MHz) (CDCl₃) 0.97(t, J=7.6Hz, 3H), 1.45(m, 2H), 1.78(m, 2H), 3.52(broad band, 2H), 3.83-4.50(a.c., 8H), 6.26(d, J=7.1Hz, 1H), 7.46(d, J=7.5Hz, 1H), 7.56(t, J=7.6Hz, 1H), 7.70(m, 2H), 8.05 (d, J=7.1Hz, 1H). | (KBr) 3200-2300 (broad band), 1648. 1609. 1483. 1259. 1005. |
| 9 | $CH_3O-$ | 3-cyano-2-methylthienyl | Base | A or E | 140-142 | (300 MHz) (CDCl₃) 3.58-4.70(broad band, 4H), 3.86(s, 3H), 3.93(m, 4H), 6.02(d, J=5.6Hz, 1H), 7.25(d, J=5.1 Hz, 1H), 7.50(d, J=5.1Hz, 1H), 8.04(d, J=5.6Hz, 1H). | (KBr) 2220. 1626. 1587. 1563. 1511. 1434. 1340. 1259. 988. |

TABLE I-continued

Structure: R1-substituted pyrimidine connected to piperazine, with the other piperazine nitrogen bearing a C(=O)R2 group.

| Example | R1 | R2 | Base or salt | METHOD | m.p. (°C.) | ¹H RMN (MHz) (Solvent) δ | IR, cm⁻¹ |
|---|---|---|---|---|---|---|---|
| 10 | $CH_3O-$ | 3-cyano-2-methylthiophen-yl | HCl | G | 136-138 | (300 MHz) (CDCl₃) 3.84(broad singlet, 4H), 4.00-4.45(a.c., 7H, (δ=4.07. s)), 6.30(d, J=6.8Hz, 1H), 7.28(d, J=5.1Hz, 1H), 7.55(d, J=5.1Hz, 1H), 8.10(J=6.8Hz, 1H). | (KBr) 3200-2300 (broad band), 2231. 1634. 1612. 1481. 1355. 1259. 1003. |
| 11 | $CH_3CH_2O-$ | 3-cyano-2-methylthiophen-yl | Base | A or E | 152-155 | (300 MHz) (CDCl₃) 1.35(t, J=7.1Hz, 3H), 3.71(broad band, 4H), 3.92(broad band, 4H), 4.31(q, J=7.1Hz, 2H), 6.00(d, J=5.6Hz, 1H), 7.25(d, J=5.1Hz, 1H), 7.50(d, J=5.1Hz, 1H), 8.04(d, J=5.6Hz, 1H). | (KBr) 2230. 1626. 1436. 1338. 1253. 1002. |
| 12 | $CH_3CH_2O-$ | 3-cyano-2-methylthiophen-yl | HCl | G | 171-174 | (300 MHz) (CDCl₃) 1.44(t, J=7.1Hz, 3H), 3.83(broad band, 4H), 4.05(m, 2H), 4.40(m, 2H), 4.49(q, J=7.1Hz, 2H), 6.27(d, J=6.7Hz, 1H), 7.28(d, J=5.1Hz, 1H), 7.55(d, J=5.1Hz, 1H), 8.07(d, J=6.7Hz, 1H). | (KBr) 3200-2300 (broad band), 2228. 1637. 1610. 1462. 1439. 1257. |
| 13 | $CH_3[CH_2]_2O-$ | 3-cyano-2-methylthiophen-yl | Base | A or E | 106-107 | (300 MHz) (CDCl₃) 0.96(t, J=7.3Hz, 3H), 1.75(m, 2H), 3.71(broad band, 4H), 3.91(broad band, 4H), 4.20(t, J=6.6Hz, 2H), 6.01(d, J=5.8Hz, 1H), 7.25(d, J=5.1Hz, 1H), 7.50(d, J=5.1Hz, 1H), 8.05(d, J=5.8Hz, 1H). | (KBr) 2230. 1628. 1582. 1560. 1436. 1255. 1003. |
| 14 | $CH_3[CH_2]_2O-$ | 3-cyano-2-methylthiophen-yl | HCl | G | 147-149 | (300 MHz) (CDCl₃) 1.02(t, J=7.3Hz, 3H), 1.83(m, 2H), 3.83(broad band, 4H), 4.06(broad band, 2H), 4.37(broad triplet, J=6.6Hz, 4H), 6.28(d, J=6.8Hz, 1H), 7.28(d, J=5.1Hz, 1H), 7.54(d, J=5.1Hz, 1H), 8.07(d, J=6.8Hz, 1H). | (KBr) 3200-2300 (broad band), 2234. 1638. 1606. 1483. 1439. 1258. 998. |
| 15 | $CH_3CH_2O-$ | 3-cyano-2-methylpyridin-yl | Base | A or C | 137-139 | (300 MHz) (CDCl₃) 1.34(t, J=7.1Hz, 3H), 3.42(m, 2H), 3.78-4.00(a.c., 6H), 4.30(q, J=7.1Hz, 2H), 5.99(d, J=5.6Hz, 1H), 7.48(dd, J=7.8Hz, J'=4.9Hz, 1H), 8.03(d, J=5.6Hz, 1H), 8.07(d, J=7.8Hz, 1H), 8.78(d, J=4.9Hz, 1H). | (KBr) 2230. 1637. 1607. 1558. 1444. 1341. 1316. 1258. 1002. |
| 16 | $CH_3CH_2O-$ | 3-cyano-2-methylpyridin-yl | HCl | G | 170-172 | (300 MHz) (CD₃OD) 1.43(t, J=7.2Hz, 3H), 3.67(broad band, 2H), 3.93(broad band, 2H), 4.03(broad singlet, 4H), 4.55(q, J=7.2Hz, 2H), 6.46(d, J=7.0Hz, 1H), 7.70(dd, J=7.8Hz, J'=5.0Hz, 1H), 8.06(d, J=7.0Hz, 1H), 8.35(d, J=7.8Hz, 1H), 8.85(m, 1H). | (KBr) 3200-2300 (broad band), 2235. 1638. 1612. 1443. 1260. 1210. 997. |
| 17 | $CH_3[CH_2]_2O$ | 3-cyano-2-methylpyridin-yl | Base | A or C | 93-95 | (300 MHz) (CDCl₃) 0.98(t, J=7.4Hz, 3H), 1.75(m, 2H), 3.43(m, 2H), 3.81-4.01(a.c., 6H), 4.19(t, J=6.7Hz, 2H), 6.01(d, J=5.6Hz, 1H), 7.48(dd, J=7.8Hz, J'=5.0Hz, 1H), 8.03(d, J=5.6Hz, 1H), 8.08(dd, J=7.8Hz, J'=1.1Hz, 1H), 8.79(dd, J=5.0Hz, J'=1.1Hz, 1H). | (KBr) 2234. 1640. 1583. 1561. 1441. 1236. 1009. |
| 18 | $CH_3[CH_2]_2O$ | 3-cyano-2-methylpyridin-yl | HCl | G | 152-155 | (300 MHz) (CDCl₃) 1.02(t, J=7.4Hz, 3H), 1.80(m, 2H), 3.63(broad band), 2H), 3.90-4.20(a.c., 4H), 4.38(m, 4H), 6.27(d, J=6.8Hz, 1H), 7.52(dd, J=7.8Hz, J=4.9Hz, 1H), 8.09(m, 2H), 8.78(d, J=4.9Hz, 1H). | (KBr) 3200-2000 (broad band), 2239. 1643. 1006. 1442. 1415. 1260. 1210. 999. |

TABLE I-continued

[Structure: pyrimidine with R1 substituent, connected to piperazine, which is connected via C(=O) to R2]

| Example | R1 | R2 | Base or salt | METHOD | m.p. (° C.) | ¹H RMN (MHz) (Solvent) δ | IR, cm⁻¹ |
|---|---|---|---|---|---|---|---|
| 19 | $CH_3CH_2O-$ | 2-cyano-3-methylpyridin-4-yl | Base | A or D | 177-178 | (300 MHz) (CDCl₃) 1.34(t, J=7.1Hz, 3H), 3.37(broad band, 2H), 3.81-3.99(a.c., 6H), 4.30(q, J=7.1Hz, 2H), 6.01(d, J=5.6Hz, 1H), 7.60(dd, J=8.0 Hz, J'=4.8 Hz, 1H), 7.84(dd, J=8.0Hz, J'=1.5Hz, 1H), 8.04(d, J=5.6Hz, 1H), 8.76(dd, J=4.8Hz, J'=1.5Hz, 1H). | (KBr) 2235. 1628. 1601. 1544. 1433. |
| 20 | $CH_3CH_2O-$ | 2-cyano-3-methylpyridin-4-yl | HCl | G | 173-176 | (300 MHz) (CDCl₃) 1.42(t, J=7.1Hz, 3H), 3.53(broad singlet, 2H), 3.95(broad singlet, 2H), 4.11(broad singlet, 2H), 4.23(broad singlet, 2H), 4.46(q, J=7.1Hz, 2H), 6.24(d, J=6.6Hz, 1H), 7.62(dd, J=7.6Hz, J'=4.7Hz, 1H), 7.84(d, J=7.6Hz, 1H), 8.05(d, J=6.6Hz, 1H), 8.78(d, J=4.7Hz, 1H). | (KBr) 3600-2300 (broad band), 2228. 1637. 1616. 1464. 1437. 1000. |
| 21 | $CH_3CH_2O-$ | 4-cyanophenyl | Base | A | 132-134 | (300 MHz) (CDCl₃) 1.34(t, J=7.1Hz, 3H), 3.40(m, 2H), 3.65-4.00(a.c., 6H), 4.29(q, J=7.1Hz, 2H), 6.00(d, J=5.9Hz, 1H), 7.52 and 7.72(System AB, $J_{AB}$=8.3Hz, 4H), 8.04(d, J=5.9Hz, 1H). | (KBr) 2228. 1623. 1554. 1430. 1265. |
| 22 | $CH_3CH_2O-$ | 4-cyanophenyl | HCl | G | 167-169 | (300 MHz) (CDCl₃) 1.44(t, J=6.8Hz, 3H), 3.50-4.35(a.c., 8H), 4.49(m, 2H), 7.51 and 7.74(System AB, $J_{AB}$=7.8Hz, 4H), 8.07(d, J=6.9Hz, 1H). | (KBr) 3200-2300 (broad band), 1628. 1483. 1457. 1343. 1262. 1213. 1007. |
| 23 | $CH_3O-$ | 3-cyano-2-methylfuran-? | Base | A or E | 139-142 | (300 MHz) (CDCl₃) 3.80(m, 4H), 3.87(s, 3H), 3.91(m, 4H), 6.03(d, J=5.6Hz, 1H), 6.73(d, J=1.7Hz, 1H), 7.54(d, J=1.7 Hz, 1H), 8.05(d, J=5.6Hz, 1H). | (KBr) 2239. 1626. 1650. 1438. 1340. 1306. 1239. 987. 794. |
| 24 | $CH_3O-$ | 3-cyano-2-methylfuran-? | HCl | G | 143-145 | (300 MHz) (CDCl₃) 3.80-4.45(a.c., 11H, (δ=4.07. s)), 6.31(d, J=6.8Hz, 1H), 6.77(s, 1H), 7.57(s, 1H), 8.11(d, J=6.8Hz, 1H). | (KBr) 3600-2300 (broad band), 2228. 1629. 1490. 1444. 1267. 1001. |
| 25 | $CH_3O-$ | 2-cyano-3-methylpyridin-4-yl | Base | A or D | 153-156 | (300 MHz) (CDCl₃) 3.37(m, 2H), 3.82-4.05(a.c., 9H, (δ=3.86. s)), 6.03(d, J=5.6Hz, 1H), 7.60(dd, J=8.0Hz, J'=4.8 Hz, 1H), 7.84(dd, J=8.0Hz, J'=1.5Hz, 1H), 8.04(d, J=5.6Hz, 1H), 8.76(dd, J=4.8Hz, J'=1.5Hz, 1H). | (KBr) 2239. 1628. 1560. 1414. 1265. 1008. 797. |
| 26 | $CH_3O-$ | 2-cyano-3-methylpyridin-4-yl | HCl | G | 152-164 | (300 MHz) (CDCl₃) 3.56(broad singlet, 2H), 3.90-4.30(a.c., 9H, (δ=4.08. s)), 6.31(d, J=7.0Hz, 1H), 7.63(dd, J=7.8 Hz, J'=4.7Hz, 1H), 7.83(m, 1H), 8.07(d, J=7.0Hz, 1H), 8.80(dd, J=4.7Hz, J'=1.5Hz, 1H). | (KBr) 3600-2300 (broad band), 2232. 1618. 1498. 1413. 1287. |
| 27 | $CH_3[CH_2]_2O-$ | 2-cyano-3-methylpyridin-4-yl | Base | A or D | 165-168 | (300 MHz) (CDCl₃) 0.97(t, J=7.3Hz, 3H), 1.74(m, 2H), 3.37(m, 2H), 3.80-4.00 (a.c., 6H), 4.19(t, J=6.8Hz, 2H), 6.01(d, J=5.9Hz, 1H), 7.60(dd, J=8.0Hz, J'=4.9Hz, 1H), 7.84(d, J=8.0Hz, 1H), 8.03 (d, J=5.9Hz, 1H), 8.76(d, J=4.9Hz, 1H). | (KBr) 2964. 2240. 1627. 1555. 1433. 1037. 1242. 1009. 790. |

TABLE I-continued

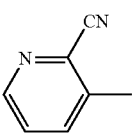

| Example | R₁ | R₂ | Base or salt | METHOD | m.p. (° C.) | ¹H RMN (MHz) (Solvent) δ | IR, cm⁻¹ |
|---|---|---|---|---|---|---|---|
| 28 | $CH_3[CH_2]_2O-$ | 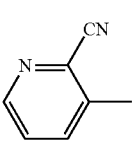 | HCl | G | 168-171 | (300 MHz) (CDCl₃) 1.02(t, J=7.3Hz, 3H), 1.81(m, 2H), 3.52(m, 2H), 3.90-4.42 (a.c., 8H), 6.24(d, J=6.6Hz, 1H), 7.62 (dd, J=7.8Hz, J'=4.8Hz, 1H), 7.83(d, J= 7.8Hz, 1H), 8.06(d, J=6.6Hz, 1H), 8.80 (m, 1H). | (KBr) 3600-2300 (broad band), 2232. 1637. 1483. 1436. 1267. 1000. |
| 29 | $CH_3[CH_2]_3O-$ | 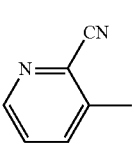 | Base | A or D | 163-164 | (300 MHz) (CDCl₃) 0.93(t, J=7.3Hz, 3H), 1.42(m, 2H), 1.70(m, 2H), 3.37(m, 2H), 3.80-4.00(a.c., 6H), 4.23(t, J=6.6Hz, 2H), 6.00(d, J=5.6Hz, 1H), 7.60(dd, J= 7.8Hz, J'=4.9Hz, 1H), 7.84(dd, J=7.8Hz, J'=1.5Hz, 1H), 8.03(d, J=5.6Hz, 1H), 8.76(dd, J=4.9Hz, J'=1.5Hz, 1H). | (KBr) 2956. 2241. 1627. 1557. 1433. 1009. 791. |
| 30 | $CH_3[CH_2]_3O-$ | 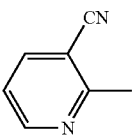 | HCl | G | 141-143 | (300 MHz) (CDCl₃) 0.95(t, J=7.3Hz, 3H), 1.44(m, 2H), 1.76(m, 2H), 3.55(broad singlet, 2H), 3.80-4.53(a.c., 8H), 6.27(d, J=6.8Hz, 1H), 7.62(dd, J=7.8Hz, J'= 4.8Hz, 1H), 7.82(m, 1H), 8.05(d, J=6.8 Hz, 1H), 8.79(dd, J=4.8Hz, J'=1.5Hz, 1H). | (KBr) 3700-2300 (broad band), 2236. 1640. 1608. 1488. 1437. 1257. 998. |
| 31 | $CH_3O-$ | 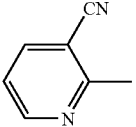 | Base | A or C | 137-139 | (300 MHz) (CDCl₃) 3.42(m, 2H), 3.80-4.06(a.c., 9H, ((δ=3.86. s)), 6.02(d, J= 5.6Hz, 1H), 7.48(dd, J=7.8Hz, J'=4.9 Hz, 1H), 8.04(d, J=5.6Hz, 1H), 8.08(d, J=7.8Hz, 1H), 8.79(d, J=4.9Hz, 1H). | (KBr) 2230. 1647. 1560. 1471. 1415. 1288. 1256. 1014. 989. |
| 32 | $CH_3O-$ | 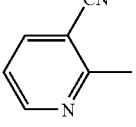 | HCl | G | 170-172 | (300 MHz) (CDCl₃) 3.65(m, 2H), 3.98(m, 2H), 4.08(broad singlet, 5H), 4.35(m, 2H), 6.30(d, J=6.8Hz, 1H), 7.54(dd, J= 8.0Hz, J'=4.9Hz, 1H), 8.10(m, 2H), 8.79 (m, 2H). | (KBr) 3600-2300 (broad band), 2231. 1630. 1604. 1482. 1406. 1354. 1265. 1009. 988. 806. |
| 33 | $CH_3[CH_2]_3O-$ | 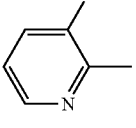 | Base | A or C | 73-75 | (300 MHz) (CDCl₃) 0.93(t, J=7.3Hz, 3H), 1.42(m, 2H), 1.70(m, 2H), 3.41(m, 2H), 3.80-4.01(a.c., 6H), 4.24(t, J=6.6Hz, 2H), 5.99(d, J=5.6Hz, 1H), 7.48(dd, J= 8.0Hz, J'=4.9Hz, 1H), 8.03(d, J=5.6Hz, 1H), 8.08(d, J=8.0Hz, 1H), 8.78(m, 1H). | (KBr) 2957. 2233. 1640. 1560. 1439. 1255. 1008. 793. |
| 34 | $CH_3[CH_2]_3O-$ | 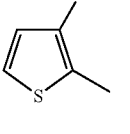 | HCl | G | 129-131 | (300 MHz) (CDCl₃) 0.97(t, J=7.3Hz, 3H), 1.46(m, 2H), 1.78(m, 2H), 3.64(broad singlet, 2H), 3.90-4.18(a.c., 4H), 4.21-4.50(a.c., 4H), 6.26(d, J=6.8Hz, 1H), 7.53(dd, J=7.8Hz, J'=4.8Hz, 1H), 8.09 (m, 2H), 8.78(d, J=4.8Hz, 1H). | (KBr) 3600-2300 (broad band), 2238. 1617. 1480. 1458. 1261. 1217. 1004. 799. |
| 35 | $CH_3[CH_2]_3O-$ | 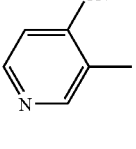 | Base | A or E | 79-82 | (300 MHz) (CDCl₃) 0.94(t, J=7.3Hz, 3H), 1.42(m, 2H), 1.70(m, 2H), 3.71(broad band, 4H), 3.91(m, 4H), 4.24(t, J=6.6 Hz, 2H), 6.00(d, J=5.9Hz, 1H), 7.25(d, J=5.2Hz, 1H), 7.49(d, J=5.2Hz, 1H), 8.03(d, J=5.9Hz, 1H). | (KBr) 2957. 2231. 1637. 1582. 1438. 1338. 1237. 1001. |
| 36 | $CH_3[CH_2]_3O-$ |  | Base | A | 97-100 | (300 MHz) (CDCl₃) 0.96(t, J=7.3Hz, 3H), 1.44(m, 2H), 1.72(m, 2H), 3.39(broad band, 2H), 3.80-4.05(a.c., 6H), 4.25(t, J= 6.6Hz, 2H), 6.03(d, J=5.7Hz, 1H), 7.61 (d, J=4.9Hz, 1H), 8.05(d, J=5.7Hz, 1H), 8.82(s, 1H), 8.85(d, J=4.9Hz, 1H). | (KBr) 2957. 2236. 1627. 1556. 1434. 1307. 1265. 1008. 790. |

TABLE I-continued

[Structure: pyrimidine with R1 at 4-position, linked via N to piperazine, linked to C(=O)R2]

| Example | R₁ | R₂ | Base or salt | METHOD | m.p. (° C.) | ¹H RMN (MHz) (Solvent) δ | IR, cm⁻¹ |
|---|---|---|---|---|---|---|---|
| 37 | $CH_3[CH_2]_3O-$ | [3-cyano-4-methyl-pyridin-yl] | Base | A | 124-127 | (300 MHz) (CDCl₃) 0.95(t, J=7.5Hz, 3H), 1.44(m, 2H), 1.72(m, 2H), 3.34(m, 2H), 3.80-4.02(a.c., 6H), 4.25(t, J=6.6Hz, 2H), 6.03(d, J=5.7Hz, 1H), 7.43(d, J=5.0Hz, 1H), 8.05(d, J=5.7Hz, 1H), 8.90 (d, J=5.0Hz, 1H), 8.96(s, 1H). | (KBr) 2956. 2238. 1630. 1602. 1556. 1434. 1308. 1265. 1012. 790. |
| 38 | $CH_3[CH_2]_3O-$ | [3-cyano-4-methyl-pyridin-yl] | HCl | G | 171-173 | (300 MHz) (CDCl₃) 0.99(t, J=7.3Hz, 3H), 1.47(m, 2H), 1.80(m, 2H), 3.54(m, 2H), 3.80-4.50(a.c., 8H), 6.30(d, J=6.7Hz, 1H), 7.44(broad band, 1H), 8.08(d, J= 6.7Hz, 1H), 8.94(d, J=4.9Hz, 1H), 9.00 (s, 1H). | (KBr) 3600-2300 (broad band), 2229. 1637. 1609. 1437. 1288. 1264. 1029. 1003. |

General Anaesthetic Activity

Studies have been performed on three species, mouse, rat and dog, following the protocols described below.

a) Anaesthetic Activity in Mice.

The anaesthetic activity was determined after intravenous (IV) administration of the product under study in three different doses (15, 10 and 5 mg/kg) in the caudal vein of the mouse. The percentage of anaesthetised animals was recorded and the average time of anaesthesia calculated. Mice were considered to be anaesthetised when losing the three reflexes: positional reflex, response to painful stimulus reflex (prick in the tail) and palpebral reflex.

The results obtained in this trial show that the products object of the invention are powerful anaesthetics as compared to one of the most widely used anaesthetics in human clinical use, propofol (table 2).

TABLE 2

Anaesthetic activity in mice

| Example | % anaesthetised (time of anaesthesia) Dose (mg/kg, iv) | | |
|---|---|---|---|
| | 15 | 10 | 5 |
| 4 | 100 (5.8') | 100 (2.6') | 0 |
| 6 | 100 (9.6') | 100 (7.6') | 90 (1.2') |
| 8 | 100 (13.3') | 100 (6.8') | 60 (0.9') |
| 12 | 100 (5.4') | 100 (1.6') | 0 |
| 14 | 100 (8.9') | 100 (2.2') | 0 |
| 18 | 100 (4.6') | 100 (3.9') | 0 |
| Propofol | 80 (1.3') | 80 (1') | 0 | b) Anaesthetic activity in dogs.

A saline solution of the product in study was perfused by means of a perfusion pump in a concentration and rate of 5 mg/ml/minute, through a cannula inserted in a vein of the front leg. The IV infusion was stopped when the animal was fully anaesthetised (loss of motor coordination, sedation, loss of response to painful stimulus—prick in the fingers of the front leg—and loss of the palpebral reflex) and the anaesthetic dose was determined (Table 3).

TABLE 3

Anaesthetic activity in dogs (IV infusion)

| Example | Anaesthetic dose (mg/kg) |
|---|---|
| 4 | 10.1 |
| 6 | 17.4 |
| 8 | 21.2 |
| 18 | 14 |
| Propofol | 21.6* |

*Animals treated with propofol only fell asleep, as they maintained the palpebral and pain reflexes.

The results obtained for dogs show that the products of the invention are clearly superior to Propofol, as they achieve full anaesthesia.

c) Anaesthetic Activity in Rats.

In this test, through the cannulated caudal vein of a rat was perfused a solution of the products under study with a concentration of 10 mg/kg. The rate of perfusion was varied to keep the rats anaesthetised for 1 hour. The total dose administered was determined, showing that the products of the invention were more active than Propofol (Table 4).

TABLE 4

Anaesthetic activity in rats:
IV infusion required to maintain full anaesthesia for 1 hour

| Example | Total dose (mg/kg) |
|---|---|
| 4 | 56.8 |
| 6 | 42.1 |
| 8 | 33.1 |
| 18 | 66.2 |
| Propofol | 67 |

Anticonvulsive Activity

This test studied the products' capacity to antagonise convulsions induced by IV injection of pentamethylentetrazol (cardiazol) at a dose of 45 mg/kg in the caudal vein of the mouse. The results show that the products under study have a greater anticonvulsive activity than propofol (Table 5).

TABLE 5

Anticonvulsive activity in mice (Convulsions due to cardiazol)

| | % Activity (mg/kg, i.p.) | | | | |
|---|---|---|---|---|---|
| Example | 80 | 40 | 20 | 10 | ED-50 |
| 2 | 100 | 73 | 36 | — | 26.1 |
| 4 | 87 | 69 | 40 | — | 25.1 |
| 6 | 93 | 63 | 69 | 0 | 24.1 |
| 8 | 100 | 70 | 56 | 25 | 25.0 |
| Propofol | 100 | 46 | 33 | — | 32.5 |

Sedative Activity

The sedative activity was studied by observing the animals' behaviour after intraperitoneal (i.p.) administration of a dose of 80 mg/kg. This observation was conducted at different times, allowing to know the sedative effect and its duration. The results obtained show that the products under study had a sedative effect, in some cases comparable to that of zolpidem and in other cases of longer duration (Table 6).

TABLE 6

Sedative activity in mice (80 mg/kg, i.p.)

| Example | 30' | 1 h | 2 h | 3 h | 4 h | 5 h | 24 h |
|---|---|---|---|---|---|---|---|
| 4 | 90 | 75 | 75 | 35 | 0 | 0 | 0 |
| 8 | 98 | 100 | 98 | 27 | 27 | 22 | 0 |
| 14 | 30 | 33 | 38 | 35 | 20 | 10 | 0 |
| 16 | 100 | 100 | 20 | 0 | 0 | 0 | 0 |
| Zolpidem | 100 | 90 | 30 | 0 | 0 | 0 | 0 |

Activity as Muscular Relaxant

The activity as muscular relaxant of the products of the invention was studied, by evaluating the effect on body tone and abdominal tone of the rats, following the method described by S. IRWIN (Gordon Res. Conf. on Medicinal Chem.,1959. p.133). The rats received the products under study in a dose of 80 mg/kg ip, and at several times after administration (½, 1, 2, 3, 4 and 5 hours) the body and abdominal tone were evaluated, comparing muscle tension to that of the control animals. The results of Table 7 show that many products have a remarkable activity as muscular relaxants, with this effect lasting longer than with propofol, which was used as the product of reference.

TABLE 7

Myorelaxant activity in the IRWIN test in rats (80 mg/kg, ip)

| | % muscular relaxation after: | | | | |
|---|---|---|---|---|---|
| Example | ½ h. | 1 h. | 2 h. | 3 h. | 4 h. | 5 h. |
| 4 | 100 | 100 | 100 | 70 | 33 | 0 |
| 8 | 100 | 100 | 100 | 0 | 0 | 0 |
| 16 | 100 | 100 | 100 | 66 | 44 | 0 |
| Propofol | 100 | 100 | 70 | 0 | 0 | 0 |

Pharmaceutical Formulations

| 1. Injectable intramuscular/intravenous (im/iv): | |
|---|---|
| Example 4 | 5 mg |
| Sodium chloride | c.s. |
| HCl 0.1 N or NaOH 0.1 N | c.s. |
| Water for injection c.s.p. | 3 mL |
| 2. Capsules | |
| Example 4 | 0.5 to 4.0 mg |
| Colloidal silicon dioxide | 0.5 mg |
| Magnesium stearate | 1.0 mg |
| Lactose c.s.p. | 100 mg |
| 3. Pills | |
| Formula A (direct compression) | |
| Example 4 | 0.5 to 4.0 mg |
| Colloidal silicon dioxide | 0.5 mg |
| Magnesium stearate | 1.0 mg |
| Sodium Croscarmelose | 3.0 mg |
| Microcrystalline cellulose | 60 mg |
| Lactose c.s.p. | 100 mg |
| Formula B (humid granulation) | |
| Example 4 | 0.5 a 4.0 mg |
| Colloidal silicon dioxide | 0.5 mg |
| Magnesium stearate | 1.0 mg |
| Povidone K-30 | 5.0 mg |
| Sodium carboximethylstarch | 5.0 mg |
| Microcrystalline cellulose | 20 mg |
| Lactose c.s.p. | 100 mg |

What is claimed is:

1. A cyanoaryl (or cyanoheteroaryl)-carbonyl-piperazinyl-pyrimidine derivative compound or a physiologically acceptable salt thereof having formula (I)

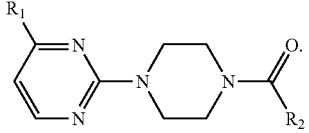

(I)

wherein $R_1$ represents $OR_3$, and wherein $R_3$ is a radical of a saturated hydrocarbon with a linear or branched chain having 1 to 4 carbon atoms; and $R_2$ is either a phenyl radical substituted by at least one cyano radical (—C≡N), or a radical of a heteroaromatic ring with 5 or 6 members substituted by at least one cyano radical (—C≡N).

2. The compound of claim 1 selected from the group consisting of:
2-[4-(2-cyanobenzoyl)-1-piperazinyl]-4-methoxypyrimidine;
2-[4-(2-cyanobenzoyl)-1-piperazinyl]-4-methoxypyrimidine hydrochloride;
2-[4-(2-cyanobenzoyl)-1-piperazinyl]-4-ethoxypyrimidine;
2-[4-(2-cyanobenzoyl)-1-piperazinyl]-4-ethoxypyrimidine hydrochloride;
2-[4-(2-cyanobenzoyl)-1-piperazinyl]-4-propoxipyrimidine;
2-[4-(2-cyanobenzoyl)-1-piperazinyl]-4-propoxipyrimidine hydrochloride;
4-butoxy-2-[4-(2-cyanobenzoyl)-1-piperazinyl]pyrimidine;
4-butoxy-2-[4-(2-cyanobenzoyl)-1-piperazinyl]pyrimidine hydrochloride;

2-[4-(3-cyano-2-thienylcarbonyl)-1-piperazinyl]-4-methoxypyrimidine;
2-[4-(3-cyano-2-thienylcarbonyl)-1-piperazinyl]-4-methoxypyrimidine hydrochloride;
2-[4-(3-cyano-2-thienylcarbonyl)-1-piperazinyl]-4-ethoxypyrimidine;
2-[4-(3-cyano-2-thienylcarbonyl)-1-piperazinyl]-4-ethoxypyrimidine hydrochloride;
2-[4-(3-cyano-2-thienylcarbonyl)-1-piperazinyl]-4-propoxipyrimidine;
2-[4-(3-cyano-2-thienylcarbonyl)-1-piperazinyl]-4-propoxipyrimidine hydrochloride;
2-[4-(3-cyano-2-pyridylcarbonyl)-1-piperazinyl]-4-ethoxypyrimidine;
2-[4-(3-cyano-2-pyridylcarbonyl)-1-piperazinyl]-4-ethoxypyrimidine monohydrochloride;
2-[4-(3-cyano-2-pyridylcarbonyl)-1-piperazinyl]-4-propoxipyrimidine;
2-[4-(3-cyano-2-pyridylcarbonyl)-1-piperazinyl]-4-propoxipyrimidine monohydrochloride;
2-[4-(2-cyano-3-pyridylcarbonyl)-1-piperazinyl]-4-ethoxypyrimidine;
2-[4-(2-cyano-3-pyridylcarbonyl)-1-piperazinyl]-4-ethoxypyrimidine monohydrochloride;
2-[4-(4-cyanobenzoyl)-1-piperazinyl]-4-ethoxypyrimidine;
2-[4-(4-cyanobenzoyl)-1-piperazinyl]-4-ethoxypyrimidine hydrochloride;
2-[4-(3-cyano-2-furylcarbonyl)-1-piperazinyl]-4-methoxypyrimidine;
2-[4-(3-cyano-2-furylcarbonyl)-1-piperazinyl]-4-methoxypyrimidine hydrochloride;
2-[4-(2-cyano-3-pyridylcarbonyl)-1-piperazinyl]-4-methoxypyrimidine;
2-[4-(2-cyano-3-pyridylcarbonyl)-1-piperazinyl]-4-methoxypyrimidine monohydrochloride;
2-[4-(2-cyano-3-pyridylcarbonyl)-1-piperazinyl]-4-propoxipyrimidine;
2-[4-(2-cyano-3-pyridylcarbonyl)-1-piperazinyl]-4-propoxipyrimidine monohydrochloride;
4-butoxy-2-[4-(2-cyano-3-pyridylcarbonyl)-1-piperazinyl]pyrimidine;
4-butoxy-2-[4-(2-cyano-3-pyridylcarbonyl)-1-piperazinyl]pyrimidine monohydrochloride;
2-[4-(3-cyano-2-pyridylcarbonyl)-1-piperazinyl]-4-methoxypyrimidine;
2-[4-(3-cyano-2-pyridylcarbonyl)-1-piperazinyl]-4-methoxypyrimidine monohydrochloride;
4-butoxy-2-[4-(3-cyano-2-pyridylcarbonyl)-1-piperazinyl]pyrimidine;
4-butoxy-2-[4-(3-cyano-2-pyridylcarbonyl)-1-piperazinyl]pyrimidine monohydrochloride;
4-butoxy-2-[4-(3-cyano-2-thienylcarbonyl)-1-piperazinyl]pyrimidine;
4-butoxy-2-[4-(4-cyano-3-pyridylcarbonyl)-1-piperazinyl]pyrimidine;
4-butoxy-2-[4-(3-cyano-4-pyridylcarbonyl)-1-piperazinyl]pyrimidine; and
4-butoxy-2-[4-(3-cyano-4-pyridylcarbonyl)-1-piperazinyl]pyrimidine monohydrochloride.

3. A method of preparing the compound of claim 1 comprising reacting an amine having formula (II):

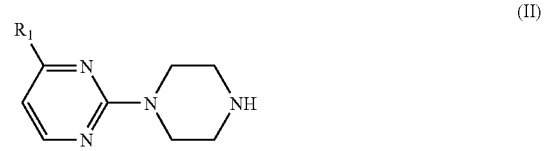

wherein $R_1$ represents an $OR_3$ radical, where $R_3$ is a radical of a saturated hydrocarbon with a linear or branched chain having 1 to 4 carbon atoms; with a carboxylic acid having formula (III) or a salt thereof:

$$R_2CO_2H \quad (III)$$

wherein $R_2$ is either a phenyl radical substituted by at least one cyano radical (—C≡N), or a radical of a heteroaromatic ring with 5 or 6 members substituted by at least one cyano radical (—C≡N).

4. A method of preparing the compound of claim 1 comprising reacting an amine having formula (II)

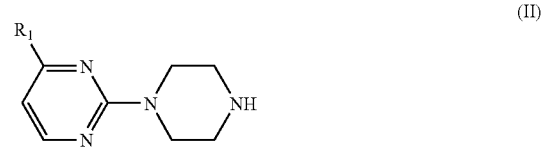

wherein $R_1$ represents an $OR_3$ radical, where $R_3$ is a radical of a saturated hydrocarbon with a linear or branched chain having 1 to 4 carbon atoms; with a derivative of carboxylic acid having formula (IV)

$$R_2COX \quad (IV)$$

where $R_2$ is either a phenyl radical substituted by at least one cyano radical (—C≡N), or a radical of a heteroaromatic ring with 5 or 6 members substituted by at least one cyano radical (—≡N); and X is selected from the group consisting of: a halogen atom, an azide group (—$N_3$), a 1-imidazolyl group and an OR—CO—$R_4$ group wherein $R_4$ is selected from the group consisting of an alkyl radical of 1 to 6 carbon atoms, an aryl radical optionally substituted with one or several halogen atoms and an $OR_5$ group where $R_5$ is an aromatic group of one or two rings substituted by one or more halogen atoms, nitro radicals, or N-succinimide.

5. A method of preparing the compound of claim 1 where $R_2$ in formula I is a phenyl radical substituted by at least one cyano radical (—≡N), comprising:

(a) reacting an amine having formula (II):

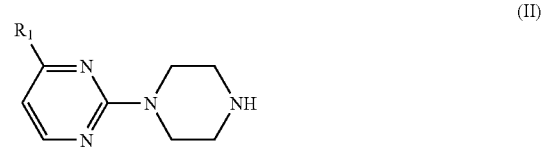

wherein $R_1$ represents an $OR_3$ radical, where $R_3$ is a radical of a saturated hydrocarbon with a linear or branched chain having 1 to 4 carbon atoms; with 3-bromophthalide to obtain an aldehyde having the formula (VI):

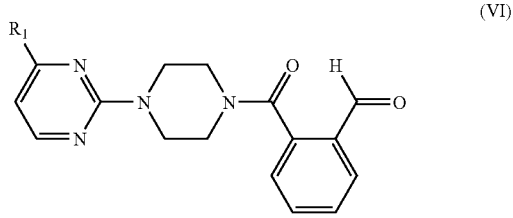

(VI)

(b) reacting said aldehyde with hydroxylamine or a salt thereof to give an oxime; and
(c) either:
(i) reacting said oxime with a dehydration reagent in the presence of Cu(II) ions; or
(ii) acylated said oxime with acetic anhydride or trifluoroacetic anhydride followed by treatment with an organic or inorganic base to result in the compound of formula I.

6. A method of preparing the compound of claim 1 where $R_2$ in formula I is either a phenyl radical substituted by at least one cyano radical (—C≡N), or a pyridyl radical substituted, at least, by one cyan radical (—C≡N), said method comprising:
(a) reacting an amine having formula (II)

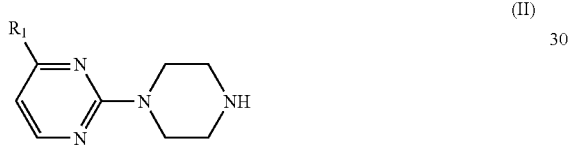

(II)

wherein $R_1$ represents an $OR_3$ radical, where $R_3$ is a radical of a saturated hydrocarbon with a linear or branched chain having 1 to 4 carbon atoms; with a compound selected from the group consisting of phthalic anhydride, phthalic acid, 2,3-pyridindicarboxylic anhydride and 2,3-pyridindicarboxylic acid to give an acid having the formula (X):

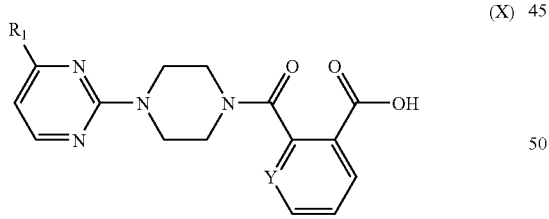

(X)

where $R_1$ represents an alkoxy radical, and Y represents a nitrogen atom or an aromatic carbon atom joined to a hydrogen atom,
(b) reacting said acid with a carbonyl group activation reagent followed by ammonia in order to obtain an amide; and
(c) reacting said amide with a dehydration reagent to result in the compound of formula I.

7. A method of preparing the compound of claim 1 where $R_2$ in formula I is a phenyl radical substituted by at least one cyano radical (—C≡N), or a pyridyl radical substituted at least by one cyan radical (—C≡N), said method comprising:

(a) reacting an amine having formula (II)

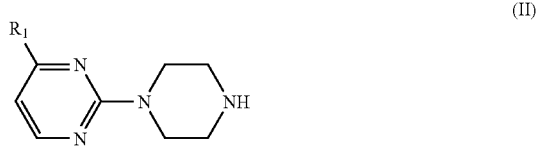

(II)

wherein $R_1$ represents an $OR_3$ radical, where $R_3$ saturated hydrocarbon with a linear or branched chain having 1 to 4 carbon atoms; with monomethyl phthalate or with 2-methoxycarbonylnicotinic acid in order to form an ester having the formula (XIII):

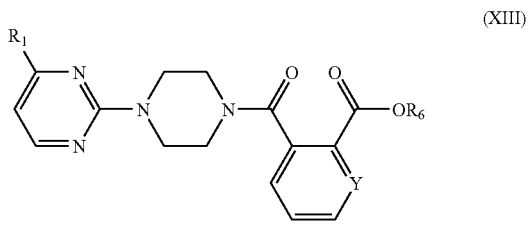

(XIII)

where $R_1$ represents an alkoxy radical, and Y represents a nitrogen atom or an aromatic carbon atom joined to a hydrogen atom and $R_6$ represents an alkyl radical.
(b) hydrolyzing said ester previously to obtain an acid;
(c) reacting said acid with a carbonyl group activation reagent followed by ammonia in order to obtain an amide; and
(d) reacting said amide with a dehydration reagent to result in the compound of formula I.

8. A method of preparing the compound of claim 1 where $R_2$ in formula I is a cyanothienyl or cyanofuryl radical, said method comprising:
(a) reacting an amine having formula (II)

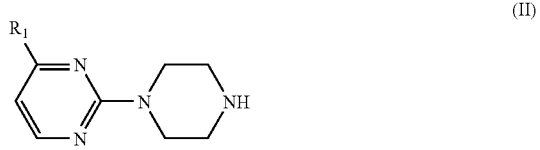

(II)

wherein $R_1$ represents an $OR_3$ radical, where $R_3$ is a radical of a saturated hydrocarbon with a linear or branched chain having 1 to 4 carbon atoms; with 1,1'-carbonyldiimidazol to form a product having the formula (XVI):

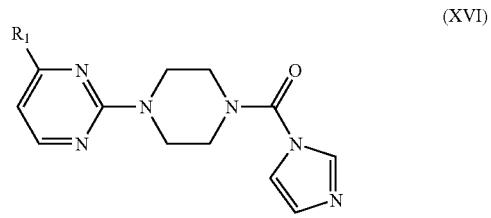

(XVI)

wherein $R_1$ represents an alkoxy radical; and (b) reaction the product of step (a) with a lithiated derivative of 3-cyanothiophene or 3-cyanofuran to result in the compound of formula I.

9. A method of preparing the compound of claim 1 comprising reacting a derivative of chloropyrimidine having formula (XVIII) with a derivative of piperazine having formula (XIX):

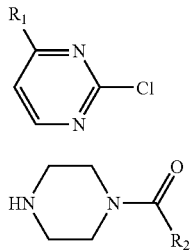

(XVIII)

(XIX)

wherein $R_1$ represents an $OR_3$ radical, where $R_3$ is a radical of a saturated hydrocarbon with a linear or branched chain having 1 to 4 carbon atoms, and $R_2$ is either a phenyl radical substituted at least by one cyan radical (—C≡N), or a radical of a heteroaromatic ring with 5 or 6 members substituted at least by one cyan radical (—C≡N).

10. A method of preparing the physiologically acceptable salts of the compound of claim 1 comprising reacting said compound with a mineral acid or an organic acid in a solvent.

11. A pharmaceutical composition comprising the compound of claim 1 or physiologically acceptable salts thereof and a pharmaceutically acceptable excipient.

12. A method of causing an effect in a subject wherein such effect is selected from the group consisting of sedative, anticonvulsant; analgesic, muscular relaxant and antimigraine effect, said method comprising administering to said subject a pharmaceutically effective amount of the compound of claim 1 or a pharmaceutically acceptable salt thereof.

13. The method of claim 12, wherein said subject is a mammal.

14. The method of claim 13, wherein said mammal is a human.

15. A method of causing a sedative effect in a subject in need thereof; said method comprising administering to said subject with a sleep disorder a pharmaceutically effective amount of the compound of claim 1 or a pharmaceutically acceptable salt thereof.

16. The method of claim 15, wherein said subject is a mammal.

17. The method of claim 16, wherein said mammal is a human.

18. A method of causing a hypnotic or general anaesthesia in a subject in need thereof comprising administering to said subject a pharmaceutically effective amount of the compound of claim 1 or a pharmaceutically acceptable salt thereof.

19. The method of claim 18, wherein said subject is a mammal.

20. The method of claim 19, wherein said mammal is a human.

* * * * *